United States Patent
Laughner et al.

(10) Patent No.: US 9,249,055 B2
(45) Date of Patent: Feb. 2, 2016

(54) PROSTHETIC IMPLANT AND METHOD FOR FORMING A PROSTHETIC IMPLANT

(75) Inventors: Lisa M. Laughner, Indianapolis, IN (US); Paul Anthony Withey, Derby (GB); Max Eric Schlienger, Napa, CA (US); Tim Pruitt, Indianapolis, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 247 days.

(21) Appl. No.: 12/853,870

(22) Filed: Aug. 10, 2010

(65) Prior Publication Data
US 2011/0035020 A1    Feb. 10, 2011

Related U.S. Application Data

(60) Provisional application No. 61/232,650, filed on Aug. 10, 2009.

(51) Int. Cl.
*A61F 2/36*    (2006.01)
*C04B 35/111*    (2006.01)
(Continued)

(52) U.S. Cl.
CPC ............ *C04B 35/111* (2013.01); *A61F 2/3094* (2013.01); *A61F 2/36* (2013.01); *A61F 2/3662* (2013.01); *C04B 35/053* (2013.01); *C04B 35/14* (2013.01); *C04B 35/486* (2013.01); *C04B 35/505* (2013.01); *A61F 2/38* (2013.01); *A61F 2/44* (2013.01); *A61F 2002/2835* (2013.01); *A61F 2002/3092* (2013.01); *A61F 2002/30733* (2013.01); *A61F 2002/30915* (2013.01); *A61F 2002/30962* (2013.01);
(Continued)

(58) Field of Classification Search
CPC ............ A61F 2/3662; A61F 2002/368; A61F 2002/3696; A61F 2002/3692
USPC ............ 623/18.11, 19.14, 20.21, 20.3, 20.31, 623/20.34, 20.35, 20.36, 22.11, 22.15, 22.4, 623/22.41, 22.46, 23.15–23.38, 623/23.44–23.46
See application file for complete search history.

(56) References Cited

U.S. PATENT DOCUMENTS 3,886,600 A    6/1975   Kahn et al.
3,938,198 A    2/1976   Kahn et al.
(Continued)

FOREIGN PATENT DOCUMENTS

DE    4421154 A1    12/1995
EP    0765644 A2    4/1997
(Continued)

OTHER PUBLICATIONS

International Search Report and Written Opinion, PCT/US2010/045040, Rolls-Royce Corporation, The International Searching Authority/US, Jan. 11, 2011.
(Continued)

*Primary Examiner* — David Isabella
*Assistant Examiner* — Suba Ganesan
(74) *Attorney, Agent, or Firm* — Duane Morris LLP

(57) ABSTRACT

One embodiment of the present invention is a unique prosthetic implant and method for making a prosthetic implant. Other embodiments include apparatuses, systems, devices, hardware, methods, and combinations for prosthetic implants. Further embodiments, forms, features, aspects, benefits, and advantages of the present application shall become apparent from the description and figures provided herewith.

33 Claims, 5 Drawing Sheets

(51) Int. Cl.
  *A61F 2/30* (2006.01)
  *C04B 35/053* (2006.01)
  *C04B 35/14* (2006.01)
  *C04B 35/486* (2006.01)
  *C04B 35/505* (2006.01)
  *A61F 2/38* (2006.01)
  *A61F 2/44* (2006.01)
  *A61F 2/28* (2006.01)
  *A61F 2/34* (2006.01)

(52) U.S. Cl.
  CPC ............... *A61F 2002/30968* (2013.01); *A61F 2002/3479* (2013.01); *A61F 2002/368* (2013.01); *A61F 2002/3692* (2013.01); *A61F 2310/00197* (2013.01); *A61F 2310/00203* (2013.01); *A61F 2310/00215* (2013.01); *A61F 2310/00239* (2013.01); *C04B 2235/6026* (2013.01)

(56) References Cited

U.S. PATENT DOCUMENTS

| | | | |
|---|---|---|---|
| 4,595,393 A | 6/1986 | Anapliotis et al. | |
| 4,608,053 A * | 8/1986 | Keller | 623/23.31 |
| 4,714,470 A | 12/1987 | Webb, Jr. et al. | |
| 4,938,770 A * | 7/1990 | Frey et al. | 623/23.15 |
| 5,092,899 A | 3/1992 | Forte | |
| 5,192,330 A | 3/1993 | Chang et al. | |
| 5,246,461 A * | 9/1993 | Tepic | 623/23.32 |
| 5,316,550 A | 5/1994 | Forte | |
| 5,365,996 A | 11/1994 | Crook | |
| D364,926 S | 12/1995 | Webb, Jr. et al. | |
| 5,571,185 A | 11/1996 | Schug | |
| 5,648,127 A | 7/1997 | Turchan et al. | |
| 5,665,118 A | 9/1997 | LaSalle et al. | |
| 5,713,410 A | 2/1998 | LaSalle et al. | |
| 5,725,586 A | 3/1998 | Sommerich | |
| 5,776,204 A | 7/1998 | Noble et al. | |
| 5,782,286 A | 7/1998 | Sommerich | |
| 6,007,581 A | 12/1999 | Noble et al. | |
| 6,042,780 A | 3/2000 | Huang | |
| 6,102,597 A | 8/2000 | Liberman | |
| 6,200,349 B1 * | 3/2001 | Naybour | 623/23.15 |
| 6,228,123 B1 | 5/2001 | Dezzani | |
| 6,355,211 B1 | 3/2002 | Huang | |
| 6,616,697 B2 | 9/2003 | Sotereanos | |
| 6,696,073 B2 | 2/2004 | Boyce et al. | |
| 6,887,278 B2 | 5/2005 | Lewallen | |
| 6,913,623 B1 | 7/2005 | Zhu | |
| 6,923,833 B2 | 8/2005 | Wasielewski | |
| 7,115,143 B1 * | 10/2006 | Michelson | 623/16.11 |
| 7,156,872 B2 | 1/2007 | Strecker | |
| 2002/0143402 A1 | 10/2002 | Steinberg | |
| 2003/0191537 A1 | 10/2003 | Wasielewski | |
| 2004/0088056 A1 | 5/2004 | Lewallen | |
| 2004/0243246 A1 | 12/2004 | Lyren | |
| 2005/0261778 A1 * | 11/2005 | Zelener et al. | 623/23.23 |
| 2006/0093646 A1 * | 5/2006 | Cima et al. | 623/23.51 |
| 2007/0203584 A1 * | 8/2007 | Bandyopadhyay et al. | 623/23.5 |
| 2007/0250045 A1 * | 10/2007 | Trieu | 604/890.1 |
| 2008/0167723 A1 | 7/2008 | Acker et al. | |
| 2009/0192609 A1 | 7/2009 | Klabunde et al. | |

FOREIGN PATENT DOCUMENTS

| | | |
|---|---|---|
| JP | 63-43657 A | 2/1988 |
| JP | 07-265341 A | 10/1995 |
| JP | H09108248 A | 4/1997 |
| JP | 2003511198 A | 3/2003 |
| JP | 2009516544 A | 4/2009 |
| WO | 0124861 A2 | 4/2001 |
| WO | 2007062057 A2 | 5/2007 |

OTHER PUBLICATIONS

European Search Report in corresponding European application (i.e., EP10810397), mailed Mar. 14, 2014 (9 pages).

Japanese Patent Office, Official Action issued in corresponding Application No. JP 2012-524788, dated Jul. 9, 2014, 8 pp.

Office Action in corresponding JP patent application (i.e., 2012-524788), issued Jun. 4, 2015 (10 pages).

* cited by examiner

US 9,249,055 B2

PROSTHETIC IMPLANT AND METHOD FOR FORMING A PROSTHETIC IMPLANT

CROSS REFERENCE TO RELATED APPLICATIONS

The present application claims the benefit of U.S. Provisional Patent Application 61/232,650, filed Aug. 10, 2009, and is incorporated herein by reference.

FIELD OF THE INVENTION

The present invention relates generally to medical devices, and more particularly to a prosthetic implant and method for making the same.

BACKGROUND

Prosthetic implants remain an area of interest. Some existing systems have various shortcomings, drawbacks, and disadvantages relative to certain applications. Accordingly, there remains a need for further contributions in this area of technology.

SUMMARY

One embodiment of the present invention is a unique prosthetic implant and method for making a prosthetic implant. Other embodiments include apparatuses, systems, devices, hardware, methods, and combinations for prosthetic implants. Further embodiments, forms, features, aspects, benefits, and advantages of the present application shall become apparent from the description and figures provided herewith.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
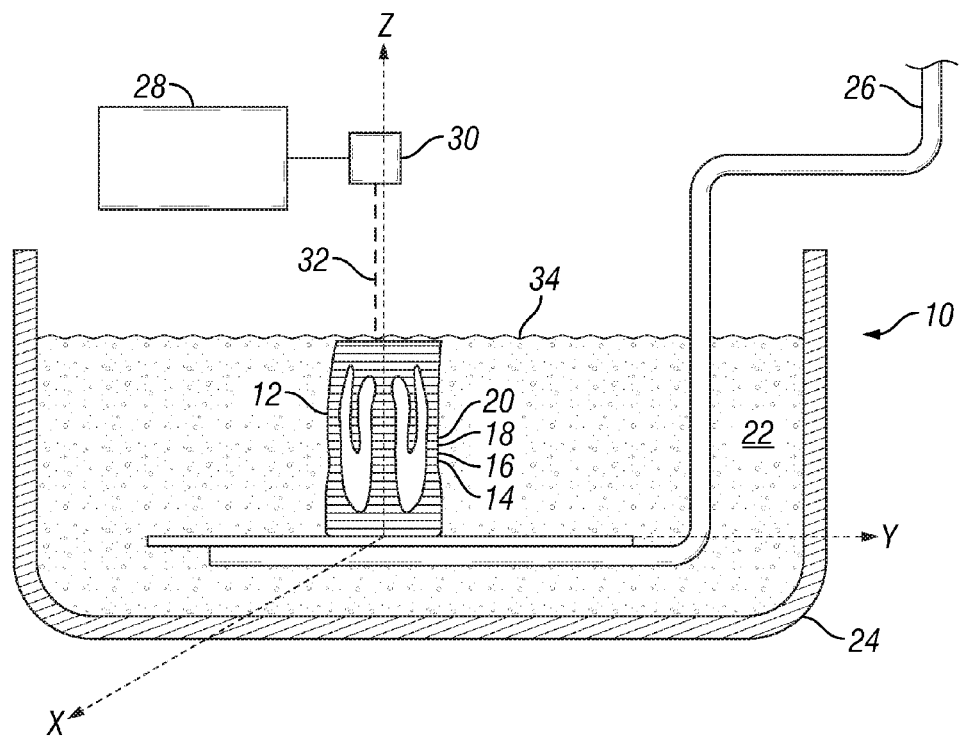
FIG. 1 is a system for freeform fabricating a prosthetic implant casting mold in accordance with an aspect of the present invention.

For purposes of promoting an understanding of the principles of the invention, reference will now be made to the embodiments illustrated in the drawings, and specific language will be used to describe the same. It will nonetheless be understood that no limitation of the scope of the invention is intended by the illustration and description of certain embodiments of the invention. In addition, any alterations and/or modifications of the illustrated and/or described embodiment(s) are contemplated as being within the scope of the present invention. Further, any other applications of the principles of the invention, as illustrated and/or described herein, as would normally occur to one skilled in the art to which the invention pertains, are contemplated as being within the scope of the present invention.

Previous prosthetic implants, such as hip implants, were heavy, stiff devices with significant mismatches in mechanical properties compared to natural bone. The mismatch in stiffness contributes significantly to the failure of implants, and can severely limit the long-term performance of previous implants, such as hip replacements, particularly in load-bearing situations. For example, in some instances, the average lifespan for primary titanium hip replacements is little more than 10 years.

The difference in the stiffness of bones versus metal means that nearly all of the load-bearing function is transferred to the metal prosthesis. Consequently, bone surrounding the implant is subjected to negligible mechanical stress, a situation known as "stress shielding". Because un-stressed cells are reabsorbed by the body, the bone holding the implant in place softens, facilitating the loosening of the device. A failure of the implant or surrounding bone typically necessitates further surgery. In accordance with some embodiments of the present invention, stress shielding effects are reduced or eliminated, thus avoiding superfluous medical intervention.

In addition, a weak interface between the implant and bone tissue can lead to "micromotion" of the implant, which is may precipitate its ultimate failure. A porous implant, e.g., an inter-connected (open) porous structure may allow bone ingrowth, reducing or eliminating the problem of micromotion and thus reducing failure rates.

In one form, embodiments of the present invention include a hollow hip stem and a method for producing the hollow hip stem via a virtual pattern casting process (VPC process), e.g., freeform fabrication of a casting mold. Some embodiments of the present invention include pins, fins, and/or a hollow lattice structures that enable a lighter weight implant that has a lower stiffness. In addition, in some embodiments, pins, fins and/or a hollow lattice structure enable custom stiffness 'tuning', wherein the stiffness depends on the selection of the type of pin and fin features and the location of the features, or on the nature of lattice structure, e.g., the sizing and placement of the lattice structure's framework members. Further, in some embodiments, pins, fins, and/or a hollow lattice structure enables bone in-growth into the device, better securing the prosthetic device inside the bone. Still further, in some embodiments, hollow channels may be cast into the device, may carry a bone growth agent, and may accommodate a biodegradable plug, which further enables bone-in-growth into the device. Also, in some embodiments, an integral core/shell mold is formed for casting the prosthetic device.

Some embodiments of the present invention include a "flexible" device design which distributes the loads, rather than concentrating them at the end of the prosthetic device, thus reducing "stress-shielding." In addition, some embodiments of the present invention also improve the device's long-term performance by providing a hollow lattice structure for bone-ingrowth, which may enhance the bone/metal interface, and may reduce or eliminate micromotion between the bone and the prosthetic implant device. In some embodiments, a pin/fin/hollow lattice structure is configured to match the implant's stiffness more closely to human bone stiffness. A reduced or matched stiffness will reduce or eliminate the stress shielding for the femur, because the device no longer translates loads to the end of the device. In some embodiments, the pin, fin and/or lattice hollow structure enables the ability to "tune" the stiffness of the device a person's bone particular bone density, e.g., by VPC processing that controls the thickness, length, and/or other parameters to adjust the stiffness of the implant relative to the characteristics of a particular patient's bone geometry and/or stiffness characteristics. Also, in some embodiments, the pin, fin and/or hollow lattice structure provides a place for bone to 'hold' on as it grows. Further, in some embodiments, the implant may carry a bone growth agent to accelerate the bone growth. For example, in one form, hollow channels are cast into the prosthetic device, filled with a bone growth agent, and then plugged, e.g., with a time-release biodegradable or resorbable plug. In this manner the prosthetic device can control release the bone growth agent over time, thus enabling a faster post-operative recovery.

In some embodiments, the pin, fin, and/or hollow lattice structure may be embodied in a hip stem or other load-bearing implant devices such as a knee, elbow, spine implants.

Referring to FIG. 1, there is schematically illustrated a non-limiting example of a freeform fabrication system 10 for freeform fabrication of a ceramic prosthetic implant mold 12 in accordance with an embodiment of the present invention. Ceramic materials contemplated herein for the implant include, but are not limited to, alumina, zirconia, silica, yttria, magnesia, and mixtures thereof. In one form, system 10 is a selective laser activation (SLA) stereolithography system. Selective laser activation is based upon a stereolithography process that utilizes resins which solidify when exposed to an energy dose. In one form, the resin includes ceramic particles disposed within a photo-polymerizable monomer(s) and/or oligomer(s), and the energy dose is a polymerizing energy dose. The present application contemplates the use of an oligomer(s) resin alone or in combination with a monomer resin. Although the present application is described with respect to a component in the form of prosthetic implant mold 12, it will be understood that the present application is also applicable to other types of materials and to other types of components. While the present application will be generally described with respect to an SLA stereolithography system, it is equally applicable to other freeform fabrication systems, such as flash cure systems and other forms of scanned cure systems.

System 10 is used to create ceramic prosthetic implant mold 12 as a three dimensional ceramic component formed of a plurality of layers, some of which are labeled as layers 14, 16, 18 and 20. In one form, stereolithography system 10 employs a ceramic loaded resin 22, and includes a resin containment reservoir 24, an elevation-changing member 26, a laser source 28 and a scanning device 30 operative to scan a laser beam 32 across elevation changing member 26. Resin containment reservoir 24 is filled with a quantity of ceramic loaded resin 22 from which mold 12 is fabricated. In one form, ceramic loaded resin 22 contains a photoinitiator. In another form, ceramic loaded resin 22 contains a dispersant, e.g., in addition to the photoinitiator. Scanning device 30 scans a laser beam 32 from laser source 28 across ceramic loaded resin 22, e.g., on a surface 34 ceramic loaded resin 22, in the desired shape to form each layer of ceramic prosthetic implant mold 12. The ceramic particles contained in ceramic loaded resin 22 ultimately form the completed mold 12.

In one form, a three dimensional coordinate system including a first axis, a second axis and a third axis is utilized as a spatial reference for the item being fabricated, e.g., ceramic mold 12. In one form, the three-dimensional coordinate system is a Cartesian coordinate system having X, Y and Z axes corresponding to the axes of stereolithography system 10. However, other three-dimensional coordinate systems are contemplated herein, including but not limited to polar, cylindrical and spherical.

In one form, prosthetic implant mold 12 is built at a build orientation angle as measured from axis Z. The build orientation angle illustrated in FIG. 1 is zero degrees. Other build orientation angles are fully contemplated herein. The three-dimensional coordinate system is aligned with the build orientation angle. In one form the three dimensional coordinate system of ceramic prosthetic implant mold 12 and stereolithography system 10 coordinate system are coextensive.

Prosthetic implant mold 12 is freeform fabricated by system 10 in layer-by-layer fashion by applying an energy dose to cure a film of ceramic-laden photo-polymerizable resin into a polymerized layer, applying a new film of the resin, and applying an energy dose sufficient to both photo-polymerize the new film of resin into a new layer and to provide an overcure to bind the new layer to the previous layer. In one form, each new resin film is formed over the topmost polymerized layer by lowering elevation changing member 26 to submerge the topmost polymerized layer in the ceramic loaded resin 22 in reservoir 24. In other embodiments, new layers of ceramic loaded resin 22 may be applied to the topmost polymerized layer using other means. The process is repeated to form a plurality of polymerized layers, i.e., layers of ceramic particles that are held together by a polymer binder, e.g., such as the illustrated layer 14, 16, 18 and 20. The successively formed cured layers ultimately form the three-dimensional shape of ceramic prosthetic implant mold 12 having the desired three-dimensional features formed therein. The three-dimensional features of prosthetic implant mold 12 include a controlled porosity distribution in portions of the mold. For example, a controlled porosity distribution may be a distribution of interconnected nodules spaced apart by a plurality of interconnected pores that are formed layer by layer as part of implant mold 12. In one example, the interconnected nodules and interconnected pores are operable to form a metal foam with an open cell structure in selected portions of the casting produced using implant mold 12. In other embodiments, a closed cell structure may be formed in the casting by controlling the porosity distribution. In another example, the controlled porosity distribution may be generated by defining a desired form, such as the desired geometric shapes, sizes and distribution of interconnected nodules and interconnected pores. The interconnected nodules and interconnected pores may be defined electronically e.g., using commercially available stereolithography computer aided design (CAD) software to generate an STL (.stl) file. The electronic definition is then supplied to system 10, whereby scanning device 30 selectively cures subsequent layers in order to yield the desired three-dimensional interconnected nodules and interconnected pores based on the STL file. The controlled porosity distribution may aid bone ingrowth into the cast implant formed using mold 12, which may reduce micromotion between the implant and the surrounding bone tissue, as well as help transfer loads between the implant and the bone tissue. The locations of controlled porosity in or on mold 12 may vary with the needs of the application.

In one form, each polymerized layer is on the order of 0.05 mm (0.002 inches) thick, e.g., as measured along the Z axis, which may be referred to as the build direction. Thinner or thicker layers may be employed in other embodiments. For example, the thickness of each layer may vary with the needs of the particular application, including the desired resolution of the finished mold 12. In some embodiments, some layers may have a greater thickness than other layers within the same mold. It should understand that there is no intention herein to limit the present application to any particular number of layers or thickness of layers. In addition, although only a prosthetic implant mold 12 is illustrated, it will be understood that a plurality of ceramic prosthetic implant molds 12 of the same and/or different configuration may be formed as a batch in system 10.

In one form, the formation of the polymerized layers includes the use of a leveling technique to level each of the layers of the photo-polymerizable ceramic loaded resin prior to receiving the energy used to polymerize the resin. Examples of leveling techniques include ultrasonic processing; time delay; and/or a mechanically assisted sweep, such as the use of a wiper blade. The present application also contemplates embodiments that do not employ active leveling techniques.

The energy dose used to polymerize and overcure each layer may be varied or otherwise controlled. In one form, the energy dose is controlled by fixing a laser 28 power and beam 32 diameter, and then controlling the laser scan speed (rate) across the resin surface. In another form, such as with a flash cure system, the laser scan speed and laser power are replaced with exposure time and lamp power. In yet another form, the parameters that control cure and overcure are lamp power and scan speed. In various embodiments, other parameters may control cure and/or overcure.

After the formation of mold 12, prosthetic implant mold 12 may be subjected to additional processing prior to use. In one form, prosthetic implant mold 12 is subjected to burnout processing and sintering to yield an integral ceramic casting mold for creating a prosthetic implant casting.

Figure 2:
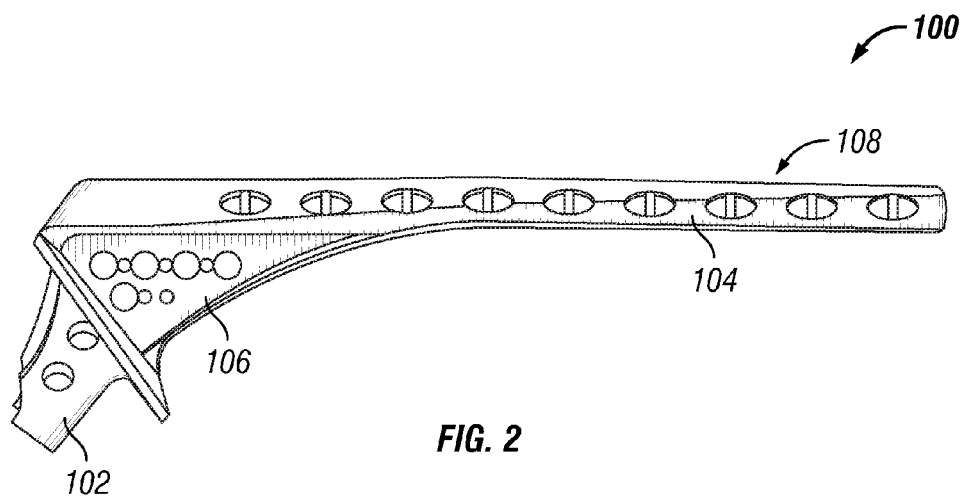
FIG. 2 illustrates a prosthetic implant in accordance with an embodiment of the present invention.
Figure 3A:
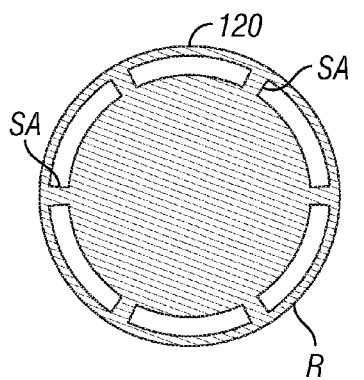
FIGS. 3A-3C illustrates one, two and three ring hollow lattice stem structures having different stiffnesses.
Figure 3B:
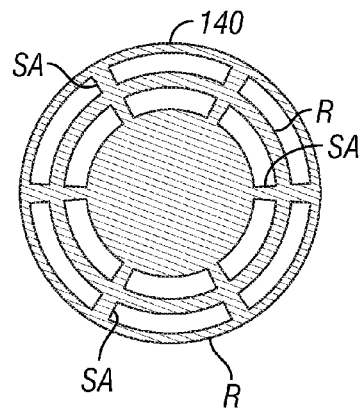
Figure 3C:
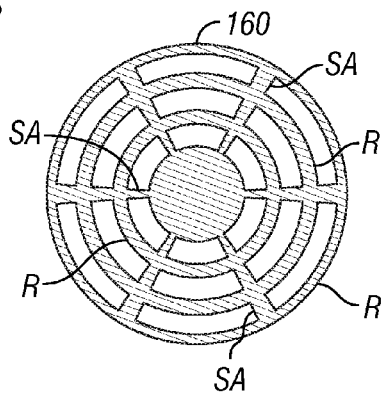

Referring now to FIG. 2, a non-limiting example of prosthetic implant 100 formed by system 10 in accordance with an embodiment of the present invention is depicted. Prosthetic implant 100 includes an interface portion 102 and a stem 104 coupled to interface portion 102. Interface portion 102 is operative to interface the prosthetic device with an other structure. In one form, interface portion 102 is a femoral head for interfacing implant 100 with a human hip socket. In other embodiments, interface portion 102 may take other forms, e.g., to interface with other biological structures. In one form, stem 104 is configured for implantation into human bone tissue, e.g., a femur. In other embodiments, stem 104 may be configured for implantation into other tissues or for interconnection with other components or devices. In one form, stem 104 is coupled to interface portion 102 via a neck portion 106. Prosthetic implant 100 includes a course pin/fin/lattice configuration 108.

Figure 4:
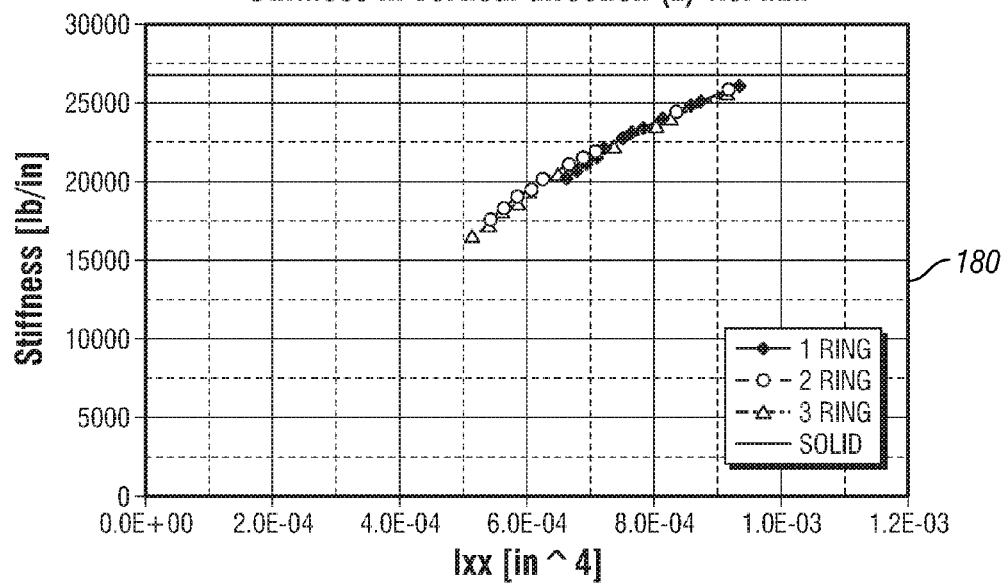
FIG. 4 is a plot illustrating the stiffness of the hollow lattice stem structures of FIGS. 3A-3C versus a solid stem.
Figure 5:
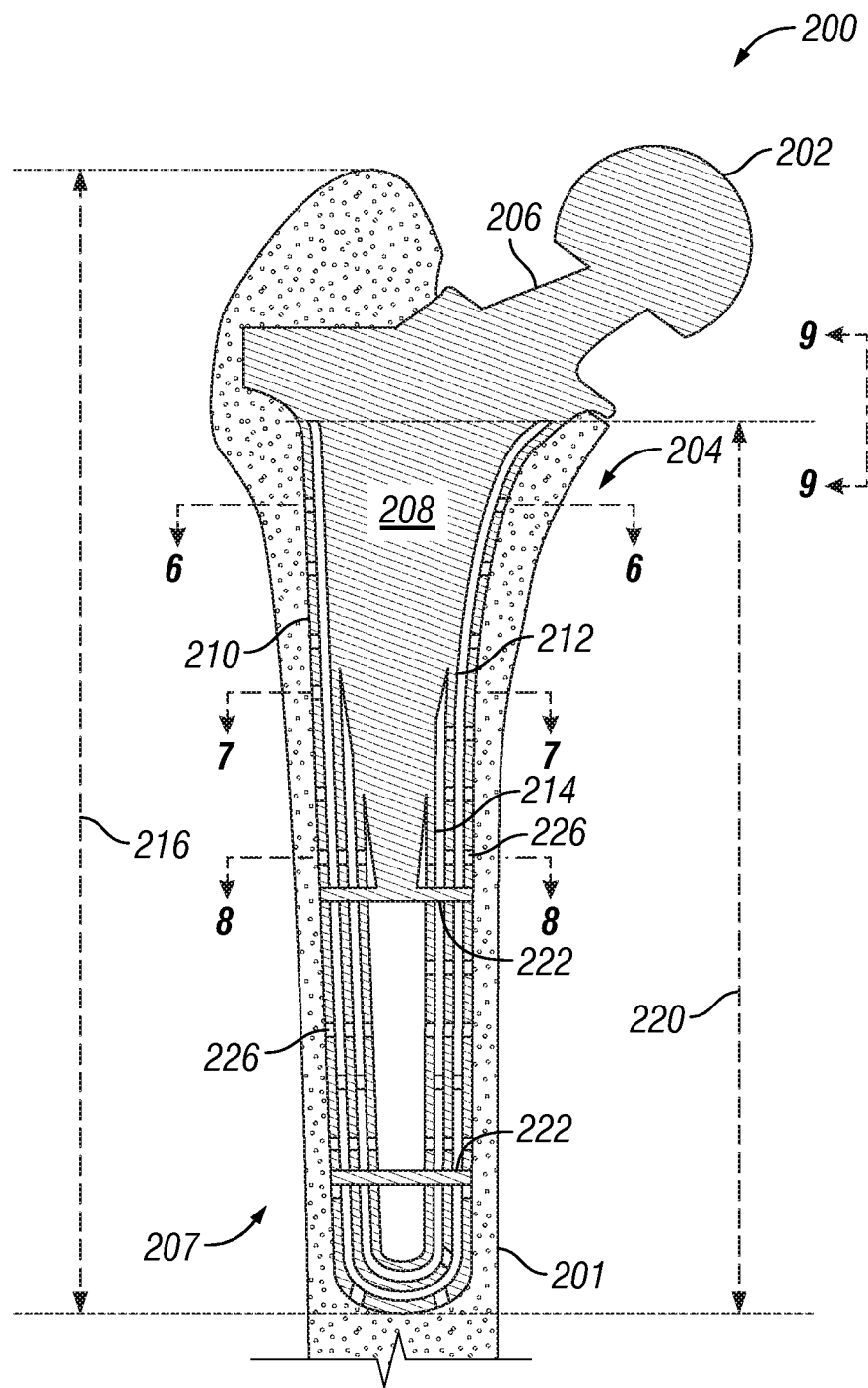
FIG. 5 is a cross section of a prosthetic implant in accordance with an embodiment of the present invention. The implant is depicted as implanted in a human femur.

Referring to FIGS. 3A-3C and FIG. 4, the inventors modeled hollow-lattice structures 120, 140 and 160 using computer aided design software to determine the amount of stiffness 'tuning' that could be adjusted, e.g., in the stem of an implant that is implanted into bone tissue, e.g., human bone tissue, such as a femur. A 30% stiffness 'tunable' adjustment was realized by modifying the thickness & number of stiffening arms, and the number of radial sections. Structure 120 is a one-ring structure, structure 140 is a two-ring structure, and structure 160 is a three-ring structure. FIG. 4 is a plot 180 depicting the stiffness of structures 120, 140 and 160 versus a solid structure. It will be understood that the number of rings R (radial sections) and the number and thickness of stiffening arms SA may be varied to achieve different stiffness values. In one form, the number of rings and/or number and/or thickness of stiffening arms varies as between different implants. In another form, the number of rings R and/or number and/or thickness of stiffening arms SA varies along the length of the stem of a particular implant in order to vary the stiffness of stem to yield different stiffness values at different points along the length of stem.

Referring now to FIGS. 5-9, another prosthetic implant in accordance with an embodiment of the present invention is depicted. Implant 200 is depicted as implanted within a human femur 201. Implant 200 includes an interface portion 202 and a stem 204 coupled to interface portion 202. Interface portion 202 is operative to interface the prosthetic device with an other structure. In one form, interface portion 202 is a femoral head for interfacing implant 200 with a human hip socket. In other embodiments, interface portion 102 may take other forms, e.g., to interface with other biological structures. In one form, stem 204 is coupled to interface portion 202 via a neck portion 206.

Figure 10:
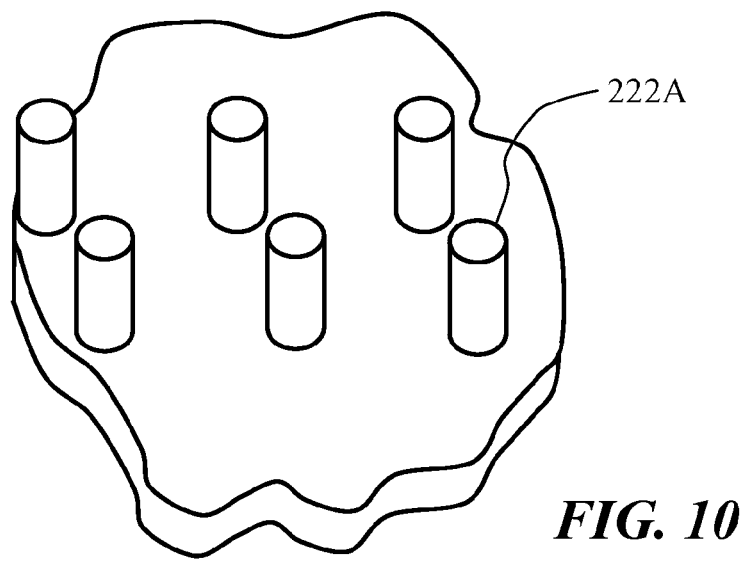
FIG. 10 illustrates pins in accordance with an aspect of an embodiment of the present invention.
Figure 11:
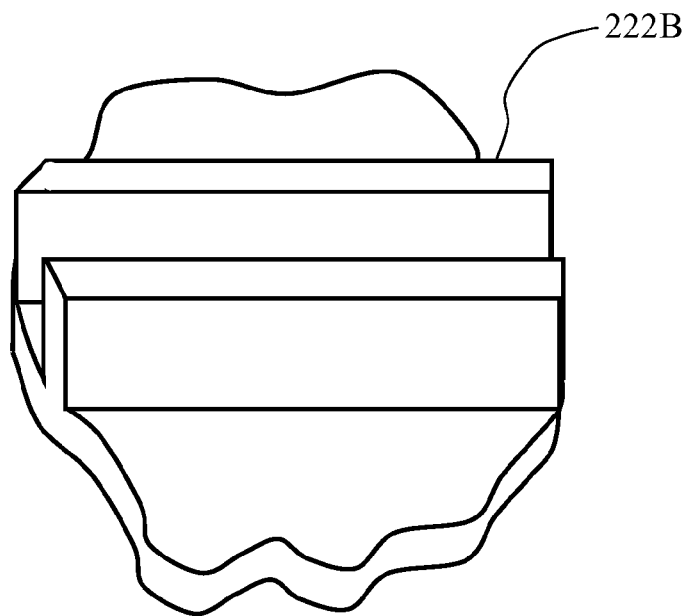
FIG. 11 illustrates fins in accordance with an aspect of an embodiment of the present invention.

Stem 204 includes body 207. Body 207 includes a core member 208, an outer ring 210, an intermediate ring 212 and an inner ring 214. Stem 204 is structured for implantation to a desired depth 216. Depth 216 may vary with the needs of the application. In one form, core member 208 is a central support member that provides support for rings 210, 212 and 214. In one form, body 207 has a length 220 approximately corresponding to the desired depth 216 of implantation. In one form, body 207 is hollow. In one form, core member 208 is solid, and outer ring 210, intermediate ring 212 and inner ring 214 are hollow lattice structures, e.g., in the form of Warren girders 225 or a strut mesh. In one form, core member 208, outer ring 210, intermediate ring 212 and inner ring 214 are coupled together via stiffening arms 222. The number and size of stiffening arms 222 may vary with the needs of the application. In one form, stiffening arms 222 are in the form of pins (e.g., pins 222A, depicted in FIG. 10) extending between one or more of rings 210, 212 and 214 and/or core member 208. In another form, stiffening arms 222 are in the form of fins (e.g., fins 222B, depicted in FIG. 11), e.g., axial or radial fins, that extend between one or more of rings 210, 212 and 214 and/or core member 208. In one form, stiffening arms 222 are integrally cast with rings 210, 212 and 214 and core member 208. In other embodiments, stiffening arms 222 may be otherwise coupled or affixed to rings 210, 212 and 214 and core member 208. In some embodiments, a plurality of protrusions extend outwardly from the body, e.g., body 207. The protrusions may extend outwardly from outer ring structure 210. The protrusions may be integrally formed with the body, and may be operative to engage the bone tissue. The protrusions may be spaced apart from each other along the length of the body. In some embodiments, the protrusions may include a plurality of pins and/or a plurality of fins, e.g., pins 222A and/or fins 222B.

Figure 6:
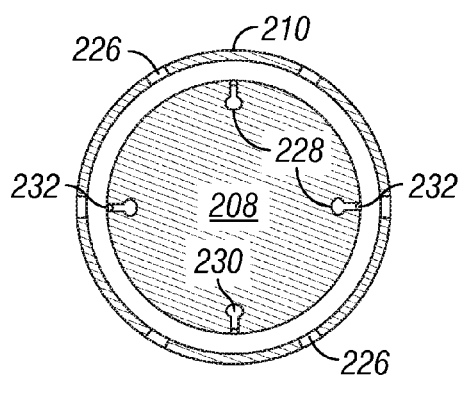
FIGS. 6-8 are cross sections taken at different locations along the length of the stem of the prosthetic implant of FIG. 5.
Figure 7:
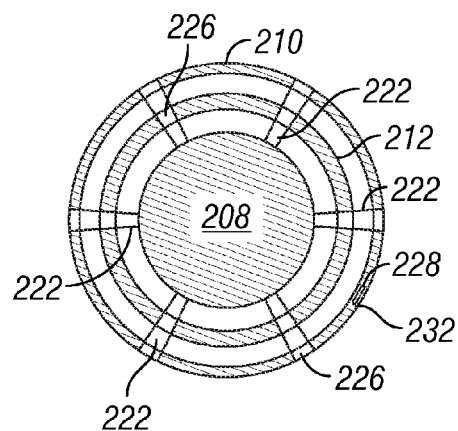
Figure 8:
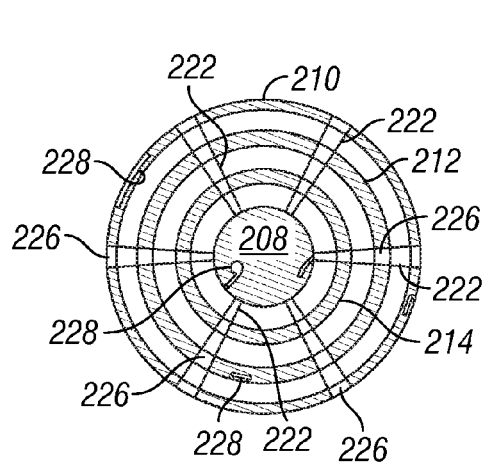
Figure 9:
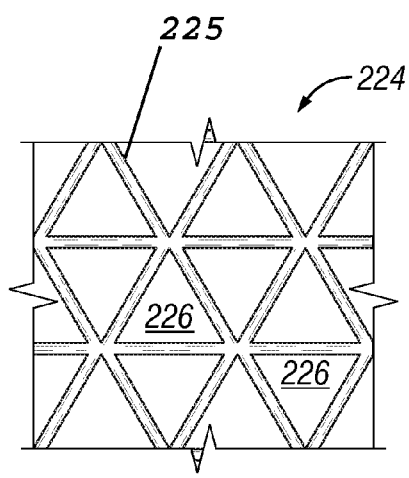
FIG. 9 is a side view of the prosthetic implant of FIG. 5 illustrating a lattice structure in accordance with an aspect of the present invention.

Although described herein as having three ring sections 210, 212 and 214, it will be understood that some embodiments may have a greater or lesser number of ring sections, and that the number of ring sections may vary along the length of the stem or may be constant along the length of the stem. In one form, each of outer ring 210, intermediate ring 212 and inner ring 214 include a lattice structure 224. In one form, each of rings 210, 212 and 214 are a lattice ring, i.e., a tubular arrangement defined by lattice structure 224, e.g., as if a sheet of a latticed material were rolled into a cylindrical or other shape. In one form, rings 210, 212 and 214 are circular in cross sectional shape, e.g., as depicted in FIGS. 6-8. In other embodiments, rings 210, 212 and 214 may have other cross sectional shapes, such as shapes corresponding to the cross section of a human femur or other bone or a non-circular opening in a bone. In some embodiments, the cross sectional size and shape of one or more of rings 210, 212 and 214 varies along the length of stem 204. In one form, lattice structure 224 is defined by openings 226. The size, shape, location and number of openings 226 may vary with the needs of the application. In one form, openings 226 extend through one or more of outer ring 210, intermediate ring 212 and inner ring 214. In the depictions of FIGS. 5-8, only a few lattice openings 226 are illustrated for purposes of clarity. In some embodiments, core member 208 also includes a lattice structure 224. In one form, core member 208 reduces in cross sectional size with increasing distance from the proximal end of core member 208 adjacent neck 206. In other embodiments, the core member may vary in cross sectional size in accordance with the needs of the application. In some embodiments, the cross sectional size of the core member may undulate along the length of core member.

In one form, each of outer ring 210, intermediate ring 212 and inner ring 214 are integral with and extend from core member 208. In other embodiments, other geometric arrangements may be employed. In one form, interface portion 202, stem portion 204 (including body 207) and neck 206 are integral cast features formed by supplying molten metal to a mold 12 having an integral shell and integral cores formed using a VPC processing system, such as system 10. In one form, a plurality of reservoirs 228 are formed into one or more of core member 208, outer ring 210, intermediate ring 212 and inner ring 214. In other embodiments, reservoirs such as reservoirs 228 may not be employed. In one form, one or more of reservoirs 228 are blind openings. In another form, one or more of reservoirs 228 are hollow channels. In one form, an agent 230, such as a bone growth agent is disposed in one or more of reservoirs 228. In one form, a plug 232, such as a resorbable plug, is employed to seal one or more reservoirs 228. In one form, plug 232 has a time-release chemical structure. In other embodiments, one or more of such agents, plugs and/or time release chemical structures may not be employed.

In one form, outer ring 210 is in contact with bone tissue during an after the implantation of implant 200. During the post operative period, bone tissue grows into openings 226 of lattice structure 224 of outer ring 210, securing implant 200 to femur 201. In one form, the flexible lattice structure 224 transmits loads to bone tissue along the length of outer ring 210. In some embodiments, bone growth continues through openings 226 in outer ring 210 to fill or partially fill the volume between outer ring 210 and intermediate ring 212. In some embodiments, the bone grown penetrates through openings 226 in intermediate ring 212 to fill or partially fill the volume between intermediate ring 212 and inner ring 214. In some embodiments, the bone grown penetrates through openings 226 in inner ring 214 to fill or partially fill the volume between inner ring 214 and core member 208. Hence, in some embodiments, stem 204 and bone tissue are interleaved/interweaved together, which increases the contact between bone tissue and implant 200, which in some embodiments may reduce micromotion between implant 200 and bone tissue and transfer loads to bone tissue, e.g., all around the periphery of stem 204.

Embodiments of the present invention include a bone-implantable prosthetic device, comprising: an interface portion operative to interface the prosthetic device with an other structure; and a stem coupled to the interface portion, wherein the stem is structured for implantation to a desired depth into a bone tissue, and wherein the stem includes: a pin, fin and/or lattice structure operative to interface with bone tissue for load transfer between the stem and the bone tissue.

In a refinement, the lattice structure is hollow.

In another refinement, the interface portion is a femoral head.

In yet another refinement, the other structure is a hip joint socket.

In still another refinement, the stem includes a hollow channel.

In yet still another refinement, the prosthetic device further includes a bone growth agent disposed in the hollow channel.

In a further refinement, the prosthetic device further includes a plug operative to seal the hollow channel.

In a yet further refinement, the plug is resorbable.

In a still further refinement, the plug is a time-release plug.

Embodiments of the present invention also include a prosthetic implant, comprising: an interface portion operative to interface with an other structure; and a stem coupled to the interface portion, wherein the stem is structured for implantation to a desired depth into a bone tissue, and wherein the stem includes: a hollow body having an outer ring structure, wherein the hollow body has a length corresponding to the desired depth of implantation, and wherein the outer ring structure includes a first plurality of openings forming an external lattice structure.

In a refinement, the openings extend through the outer ring structure, thereby exposing an interior of the hollow body to ingrowth of the bone tissue.

In another refinement, the external lattice structure is defined by a strut mesh.

In yet another refinement, the external lattice structure is defined by a Warren girder.

In still another refinement, a strut structure of the external lattice structure is tuned to achieve a stiffness of the hollow body corresponding to that of human bone tissue.

In yet still another refinement, the implant further includes a blind opening

In a further refinement, the blind opening is in the outer ring structure.

In a yet further refinement, the implant includes a bone growth agent disposed in the blind opening.

In a still further refinement, the implant includes a plug operative to seal the blind opening.

In a yet still further refinement, the plug is resorbable.

In an additional refinement, the plug is a time-release plug.

In another refinement, the implant includes an inner ring structure disposed in the hollow body inward of the outer ring structure, wherein the inner ring structure includes a second plurality of openings forming an internal lattice structure.

In yet another refinement, the inner ring structure is coupled to the outer ring structure at a plurality of locations between a distal end of the inner ring structure and a proximal end of the inner ring structure.

In still another refinement, the implant includes an intermediate ring structure disposed in the hollow body inward of the outer ring structure and outward of the inner ring structure, wherein the intermediate ring structure includes a third plurality of openings forming an intermediate lattice structure.

In yet still another refinement, the intermediate ring structure is coupled to the outer ring structure and to the inner ring structure at a plurality of locations between a distal end of the intermediate ring structure and a proximal end of the intermediate ring structure.

In a further refinement, the implant further includes a central support member disposed in the hollow body inward of the inner ring structure.

In a yet further refinement, the central support member is coupled to the inner ring structure at a plurality of locations a distal end of the inner ring structure and a proximal end of the inner ring structure.

In a still further refinement, the implant further includes a plurality of stiffening arms.

In a yet still further refinement, a number of the stiffening arms is selected to tune a stiffness of the stem to match the stiffness of human bone tissue.

In an additional refinement, a thickness of the stiffening arms is selected to tune a stiffness of the stem to match the stiffness of human bone tissue.

In another refinement, the implant further includes a plurality of radial sections.

In yet another refinement, a number of the radial sections is selected to tune a stiffness of the stem to match the stiffness of human bone tissue.

In still another refinement, a central support member disposed in the hollow body inward of the outer ring structure.

In yet still another refinement, the central support member is coupled to the outer ring structure at a plurality of locations a distal end of the outer ring structure and a proximal end of the outer ring structure.

Embodiments of the present invention also include a prosthetic implant, comprising: an interface portion operative to interface with an other structure; and a stem coupled to the interface portion, wherein the stem is structured for implantation to a desired depth into a bone tissue, and wherein the stem includes: a body having a length corresponding to the desired depth of implantation; and a plurality of protrusions extending outwardly from the body and spaced apart from each other along the length of the body, wherein the protrusions are integrally formed with the body and are operative to engage the bone tissue.

In a refinement, the body is hollow.

In another refinement, the plurality of protrusions includes a plurality of pins.

In yet another refinement, the plurality of protrusions includes a plurality of fins.

In still another refinement, the body includes an outer ring structure, and wherein the protrusions extend outward from the outer ring structure.

In yet still another refinement, the body includes a central support member disposed in the body inward of the outer ring structure.

Embodiments of the present invention also include a method of forming a prosthetic implant, comprising: freeform fabricating a ceramic mold having an integral core and integral shell, the ceramic mold structured to yield a cast prosthetic implant; sintering the ceramic mold; supplying a molten alloy to the sintered mold; and removing the ceramic mold to yield the cast prosthetic implant.

In a refinement, the method includes fabricating the ceramic mold to incorporate the features of any of the above mentioned features.

Embodiments of the present invention also include a method of forming a prosthetic implant, comprising: electronically defining a ceramic mold having an integral core and integral shell for casting a prosthetic implant; freeform fabricating the ceramic mold using the electronic definition; supplying a molten alloy to the ceramic mold; solidifying the molten alloy; and leaching the ceramic mold with integral core to yield a cast prosthetic implant.

In a refinement, the method includes fabricating the ceramic mold to incorporate the features of any of the above mentioned features.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A bone-implantable prosthetic device, comprising:
   an interface portion operative to interface the bone-implantable prosthetic device with an other structure; and
   a stem coupled to said interface portion, wherein the stem is structured for implantation to a desired depth into a bone tissue, and wherein the stem includes:
   a metallic body having a length corresponding to the desired depth of implantation; wherein said metallic body includes a support structure and a hollow pin, fin and/or lattice structure formed as a unitary structure and configured to transfer load between said stem and the bone tissue, wherein said pin, fin and/or lattice structure includes an outer ring shape that is integral with, disposed radially outward of, and fully encircles said support structure such that an offset is provided to create a space between the outer ring shape and the support, said pin, fin and/or lattice structure further including an inner ring shape that is integral with and fully encircles said support structure, the inner ring shape being disposed radially inward of the outer ring shape, and said pin, fin and/or lattice structure further including an intermediate ring shape that is integral with and fully encircles said support structure, the intermediate ring shape being disposed radially inward of the outer ring shape and outward of the inner ring shape.

2. The bone-implantable prosthetic device of claim 1, wherein the interface portion is a femoral head.

3. The bone-implantable prosthetic device of claim 2, wherein the other structure is a hip joint socket.

4. The bone-implantable prosthetic device of claim 1, wherein said stem includes a hollow channel.

5. The bone-implantable prosthetic device of claim 4, further comprising a bone growth agent disposed in said hollow channel.

6. The bone-implantable prosthetic device of claim 5, further comprising a plug operative to seal said hollow channel.

7. The bone-implantable prosthetic device of claim 6, wherein said plug is resorbable.

8. The bone-implantable prosthetic device of claim 6, wherein said plug is a time-release plug.

9. The prosthetic implant of claim 1, wherein the ring shape extends past an end of the support structure and to the desired depth of implantation such that the support structure fails to reach the desired depth of implantation.

10. A prosthetic implant, comprising:
an interface portion operative to interface with an other structure; and
a stem coupled to said interface portion, wherein the stem is structured for implantation to a desired depth into a bone tissue, and wherein the stem includes:
a hollow body having a metallic outer ring structure, wherein the hollow body has a length corresponding to a desired depth of implantation, and wherein said outer ring structure fully encircles a central support member said hollow body and includes a first plurality of openings forming a metallic external lattice structure;
a metallic inner ring structure disposed in said hollow body inward of said outer ring structure, wherein said inner ring structure includes a second plurality of openings forming a metallic internal lattice structure;
a metallic intermediate ring structure disposed in said hollow body inward of said outer ring structure and outward of said inner ring structure, wherein said intermediate ring structure includes a third plurality of openings forming a metallic intermediate lattice structure; and
the central support member being integral with and disposed within said hollow body radially inward of said outer ring structure such that an offset is provided to create a space between the outer ring structure and the central support member.

11. The prosthetic implant of claim 10, wherein the openings extend through the outer ring structure to expose an interior of the hollow body to ingrowth of the bone tissue.

12. The prosthetic implant of claim 10, wherein the external lattice structure is defined by a strut mesh.

13. The prosthetic implant of claim 10, wherein the external lattice structure is defined by a Warren girder.

14. The prosthetic implant of claim 10, wherein a strut structure of the external lattice structure is tuned to achieve a stiffness of said hollow body corresponding to that of human bone tissue.

15. The prosthetic implant of claim 10, further comprising a blind opening in said outer ring structure.

16. The prosthetic implant of claim 15, further comprising at least one of:
a bone growth agent disposed in said blind opening; and
a plug operative to seal said blind opening.

17. The prosthetic implant of claim 16, wherein said plug is at least one of a resorbable and a time-release plug.

18. The prosthetic implant of claim 16, further comprising a second blind opening in said intermediate ring structure.

19. The prosthetic implant of claim 18, further comprising at least one of:
a bone growth agent disposed in said second blind opening; and
a plug operative to seal said second blind opening.

20. The prosthetic implant of claim 10, wherein said inner ring structure is coupled to said outer ring structure at a plurality of locations between a distal end of said inner ring structure and a proximal end of said inner ring structure.

21. The prosthetic implant of claim 10, wherein said intermediate ring structure is coupled to said outer ring structure and to said inner ring structure at a plurality of locations between a distal end of said intermediate ring structure and a proximal end of said intermediate ring structure.

22. The prosthetic implant of claim 10, wherein said central support member is disposed in said hollow body inward of said inner ring structure, and wherein said central support member is coupled to said inner ring structure at a plurality of locations at a distal end of said inner ring structure and a proximal end of said inner ring structure.

23. The prosthetic implant of claim 10, further comprising a plurality of stiffening arms, wherein a number of said stiffening arms is selected to tune a stiffness of said stem to match the stiffness of human bone tissue.

24. The prosthetic implant of claim 23, wherein a thickness of said stiffening arms is selected to tune a stiffness of said stem to match the stiffness of human bone tissue.

25. The prosthetic implant of claim 10, further comprising a plurality of radial sections, wherein a number of said radial sections is selected to tune a stiffness of said stem to match the stiffness of human bone tissue.

26. The prosthetic implant of claim 10, wherein said central support member is coupled to said outer ring structure at a plurality of locations at a distal end of said outer ring structure and a proximal end of said outer ring structure.

27. A prosthetic implant, comprising:
an interface portion operative to interface with an other structure; and
a stem coupled to said interface portion, wherein the stem is structured for implantation to a desired depth into a bone tissue, and wherein the stem includes:
a metallic body having a length corresponding to a desired depth of implantation, wherein said metallic body includes a core member extending at least a portion of said length corresponding to the desired depth of implantation; an outer ring structure formed integrally with said core member and having said length corresponding to the desired depth of implantation, wherein said outer ring structure is disposed radially outward of and fully encircles said core member such that a space is created between said outer ring structure and said core; and wherein the outer ring structure has a first plurality of openings that form an external lattice structure; an inner ring structure formed integrally with said core member and disposed radially inward of said outer ring structure, wherein said inner ring structure includes a second plurality of openings that form an internal lattice structure; and an intermediate ring structure formed integrally with said core member disposed radially inward of said outer ring structure and outward of said inner ring structure, wherein said intermediate ring structure includes a third plurality of openings that form an intermediate lattice structure; and
a plurality of metallic protrusions extending outwardly from said body and spaced apart from each other along the length of said body, wherein said protrusions are integrally formed with said body and are operative to engage the bone tissue.

28. The prosthetic implant of claim 27, wherein said body is hollow.

29. The prosthetic implant of claim 27, wherein said plurality of protrusions includes a plurality of pins and/or a plurality of fins.

30. The prosthetic implant of claim 27, wherein said protrusions extend outward from said outer ring structure.

31. The prosthetic implant of claim 30, wherein said core member is a central support member disposed in said body inward of said outer ring structure.

32. A method of forming a prosthetic implant, comprising:
freeform fabricating a ceramic mold having an integral core and integral shell, said ceramic mold structured to yield a cast prosthetic implant;
sintering the ceramic mold;
supplying a molten alloy to the sintered mold; and removing the ceramic mold to yield the cast prosthetic implant;

wherein the cast prosthetic implant comprises:
- an interface portion operative to interface with an other structure; and
- a stem coupled to said interface portion, wherein the stem is structured for implantation to a desired depth into a bone tissue, and wherein the stem includes:
  - a hollow body having a metallic outer ring structure, wherein the hollow body has a length corresponding to a desired depth of implantation, and wherein said outer ring structure fully encircles a central support member and includes a first plurality of openings forming a metallic external lattice structure;
  - a metallic inner ring structure disposed in said hollow body inward of said outer ring structure, wherein said inner ring structure includes a second plurality of openings forming a metallic internal lattice structure;
  - a metallic intermediate ring structure disposed in said hollow body inward of said outer ring structure and outward of said inner ring structure, wherein said intermediate ring structure includes a third plurality of openings forming a metallic intermediate lattice structure; and
  - the central support member being integral with and disposed within said hollow body radially inward of said outer ring structure such that an offset is provided to create a space between the outer ring structure and the central support member.

33. A method of forming a prosthetic implant, comprising:

electronically defining a ceramic mold having an integral core and integral shell for casting a prosthetic implant;

freeform fabricating the ceramic mold using the electronic definition;

supplying a molten alloy to the ceramic mold;

solidifying the molten alloy; and leaching the ceramic mold to yield a cast prosthetic implant;

wherein the cast prosthetic implant comprises:
- an interface portion operative to interface with an other structure; and
- a stem coupled to said interface portion, wherein the stem is structured for implantation to a desired depth into a bone tissue, and wherein the stem includes:
  - a hollow body having a metallic outer ring structure, wherein the hollow body has a length corresponding to a desired depth of implantation, and wherein said outer ring structure fully encircles a central support member and includes a first plurality of openings forming a metallic external lattice structure;
  - a metallic inner ring structure disposed in said hollow body inward of said outer ring structure, wherein said inner ring structure includes a second plurality of openings forming a metallic internal lattice structure;
  - a metallic intermediate ring structure disposed in said hollow body inward of said outer ring structure and outward of said inner ring structure, wherein said intermediate ring structure includes a third plurality of openings forming a metallic intermediate lattice structure; and the central support member being integral with and disposed within said hollow body radially inward of said outer ring structure such that an offset is provided to create a space between the outer ring structure and the central support member.

* * * * *